United States Patent [19]

Barney et al.

[11] 4,450,843
[45] May 29, 1984

[54] MINIATURE BIOFEEDBACK INSTRUMENT

[75] Inventors: George M. Barney, Dallas; Paul R. Michaelis, Garland, both of Tex.

[73] Assignee: Texas Instruments Incorporated, Dallas, Tex.

[21] Appl. No.: 209,564

[22] Filed: Nov. 24, 1980

[51] Int. Cl.$^3$ .............................................. A61B 5/02
[52] U.S. Cl. .................................. 128/690; 128/706; 128/736; 128/670
[58] Field of Search ............................ 128/670-671, 128/690, 689, 698, 706, 736

[56] References Cited

U.S. PATENT DOCUMENTS

| | | | |
|---|---|---|---|
| 3,398,736 | 4/1968 | Brant et al. | 128/706 |
| 3,871,362 | 3/1975 | Dunegan | 128/670 |
| 4,312,358 | 1/1982 | Barney | 128/670 |

FOREIGN PATENT DOCUMENTS

| | | | |
|---|---|---|---|
| 2531242 | 1/1976 | Fed. Rep. of Germany | 128/670 |
| 7503285 | 8/1976 | France | 128/671 |
| 53-32765 | 3/1978 | Japan | 128/690 |
| WO79/00962 | 5/1980 | PCT Int'l Appl. | 128/690 |
| 2021779 | 12/1979 | United Kingdom | 128/670 |
| 2052050 | 1/1981 | United Kingdom | 128/690 |

Primary Examiner—Edward M. Coven
Assistant Examiner—Max F. Hindenburg
Attorney, Agent, or Firm—William E. Hiller; James T. Comfort; Melvin Sharp

[57] ABSTRACT

A compact, miniature instrument for providing biofeedback information of interest to a user. The instrument is comprised of a wrist-watch size unit, which includes a temperature sensor for sensing the user's external skin temperature and a finger-mountable unit, which includes a heart beat sensor for sensing the user's heart beat. Processing circuitry is provided for computing various biofeedback parameters of interest to the user, including pulse rate, time rate of change in pulse rate and time rate of change in external skin temperature. Timekeeping circuitry is provided for keeping track of various time-related parameters, such as time of day and calendar date. A display is provided for selectively displaying biofeedback and time-related information to the user.

5 Claims, 4 Drawing Figures

MINIATURE BIOFEEDBACK INSTRUMENT

BACKGROUND OF THE INVENTION

This invention relates to physiological monitoring instruments and in particular to a biofeedback instrument for sensing a user's external skin temperature and heart beat and providing temperature and heart beat-related biofeedback information for the user.

Instruments for measuring and monitoring physiological parameters such as heart beat and body temperature are known in the art. Such instruments, however, are typically AC powered, analog instruments comprised of a large number of electronic components contained in a relatively large table or desk-mounted unit. A plurality of electrical wires extend from the main unit for attachment to various parts of a patient's body to measure physiological and biofeedback parameters, such as body temperature and heart beat. Because of the relatively large size and high power consumption, such instruments are typically used only in the confines of a medical facility or the like and are not suitable for day to day usage by an active individual.

Skin temperature and pulse rate are excellent indicators of the level of physiological and emotional stress being experienced by an individual. Typically, when one is under stress, blood is diverted from his skin to his muscles, thereby causing his skin temperature to decrease, and his heart beats faster, resulting in an increased pulse rate. Biofeedback instruments known in the art provide indications of skin temperature and pulse rate, but do not provide the user with an indication of how his skin temperature and pulse rate are changing with time. Time rates of change in biofeedback parameters such as skin temperature and pulse rate are significant because they provide the user with an indication of how well he is progressing in being able to consciously relax and reduce stress.

SUMMARY OF THE INVENTION

It is therefore one object of the invention to provide a compact, miniature biofeedback instrument.

It is another object of the invention to provide a low power biofeedback instrument which is capable of being operated by a small battery power supply.

It is yet another object of the invention to provide a wrist-watch size biofeedback instrument which can be worn conveniently by a user on his wrist.

It is still another object of the invention to provide the user of the biofeedback instrument with an indication of how well he is progressing in being able to consciously relax and reduce stress.

It is a further object of the invention to provide a biofeedback instrument that computes time rates of change of various biofeedback parameters, including skin temperature and pulse rate.

It is still a further object of the invention to provide an instrument which keeps track of time-related information, including time of day and calendar date, in addition to biofeedback information.

These and other objects are accomplished in accordance with the present invention wherein a biofeedback instrument is provided which is comprised of temperature sensing means for detecting the user's external skin temperature; processing means, including means for keeping track of elapsed time and means responsive to the detected skin temperatures and to elapsed time information for determining a time rate of change in the user's skin temperature over a predetermined time interval; and output indicator means for providing a real-time indication to the user of his external skin temperature and the time rate of change in his skin temeprature, thereby apprising the user of the level of physiological stress he is experiencing and his progress in reducing the stress.

In one embodiment, the instrument further includes heart beat sensing means for detecting the user's heart beats. The processing means includes means responsive to the detected heart beats and elapsed time information for determining the user's pulse rate and time rate of change in pulse rate over a predetermined time interval. In addition to periodically determining current time rates of change in the user's skin temperature and pulse rate, the processing means further determines average values for the time rates of change in skin temperature and pulse rate over a selected monitoring period and compares these average values with predetermined reference values for the time rates of change in skin temperature and pulse rate to determine the respective differences therebetween, thereby giving the user an indication of his relative progress in being able to relax and reduce stress.

In a preferred embodiment, the biofeedback instrument is comprised of a wrist-mountable unit containing the temperature sensing means, processing means and output indicator means and a finger-mountable unit containing the heart beat sensing means, the finger-mountable unit being electrically coupled to the wrist-mountable unit. The temperature sensing means is preferably a thermistor, the electrical resistance of which is inversely proportional to skin temperature, and the heart beat sensing means is preferably a piezoelectric transducer. The thermistor is positioned in contact with one of the user's wrists to detect skin temperature and the piezoelectric transducer is positioned in contact with one of the user's finger to sense pulses of blood resulting from the user's heart beats. The processing means is preferably comprised of analog to digital (A/D) converter means for converting a first analog electrical signal indicative of skin temperature and a second analog electrical signal indicative of heart beat into corresponding first and second digital signals and digital processing means having timekeeping circuit means for keeping track of elapsed time. The digital processor means is responsive to the first and second digital signals for determining the user's pulse rate and the time rates of change in the user's skin temperature and pulse rate. The output indicator means is preferably comprised of first and second digital displays, the first display for displaying temperature-related biofeedback parameters and the second display for displaying heart beat-related biofeedback parameters. When the digital processor means is not engaged in a processing temperature and heart beat information, it provides a plurality of time-related parameters, including time of day and calendar date, for display on the first and second digital displays.

In another aspect of the invention a miniature, battery-operable biofeedback instrument is provided. The instrument is comprised of a wrist-watch size casing; temperature sensing means for determining a user's external skin temperature; processing means responsive to the detected skin temperatures for determining a plurality of temperature-related biofeedback parameters; and output indicator means for selectively providing a real-time indication to the user of determined biofeedback parameters. The temperature sensing means, processing means and indicator means are contained within the wrist-watch size casing and are operable by means of a miniature battery power supply mountable within the casing. In one embodiment, the biofeedback instrument further includes heart beat sensing means for detecting the user's heart beat. The processing means is responsive to the detected heart beats for determining heart beat-related biofeedback parameters. In another embodiment the instrument further includes a 3 volt battery power supply to provide electrical power for the operation of the instrument.

In a preferred embodiment the temperature sensing means is comprised of a thermistor and the heart beat sensing means is comprised of a piezoelectric transducer. The thermistor is positioned in contact with one of the user's wrists for measuring his external skin temperature and the piezoelectric transducer is positioned in contact with one of the user's fingers to sense pulses of the user's blood resulting from heart beats. The processing means is comprised of low power A/D converter means and a digital processor means having timekeeping circuit means for keeping track of elapsed time. To achieve low power and miniaturization, the A/D converter means is a switch capacitor A/D converter comprised of CMOS circuitry, which consumes on the order of 50 microamps of electrical current during peak operation. The digital processor means is a microcomputer comprised of CMOS circuitry, which consumes on the order of 250 microamps of electrical current when fully engaged in processing information and on the order of 14 microamps of current when engaged only in timekeeping operations.

The biofeedback instrument of the present invention provides a compact, portable instrument, which can be conveniently and inconspicuously used by an individual to keep him apprised of the level of physiological and emotional stress he is experiencing and the progress he is making in being able to consciously relax and reduce the stress. The instrument can also be used as a wrist watch when biofeedback information is not desired. The low power characteristics of the instrument make it compatible with a miniature battery power supply, which is mountable within the wrist-watch size casing of the instrument.

DETAILED DESCRIPTION OF A PREFERRED EMBODIMENT

Figure 1:
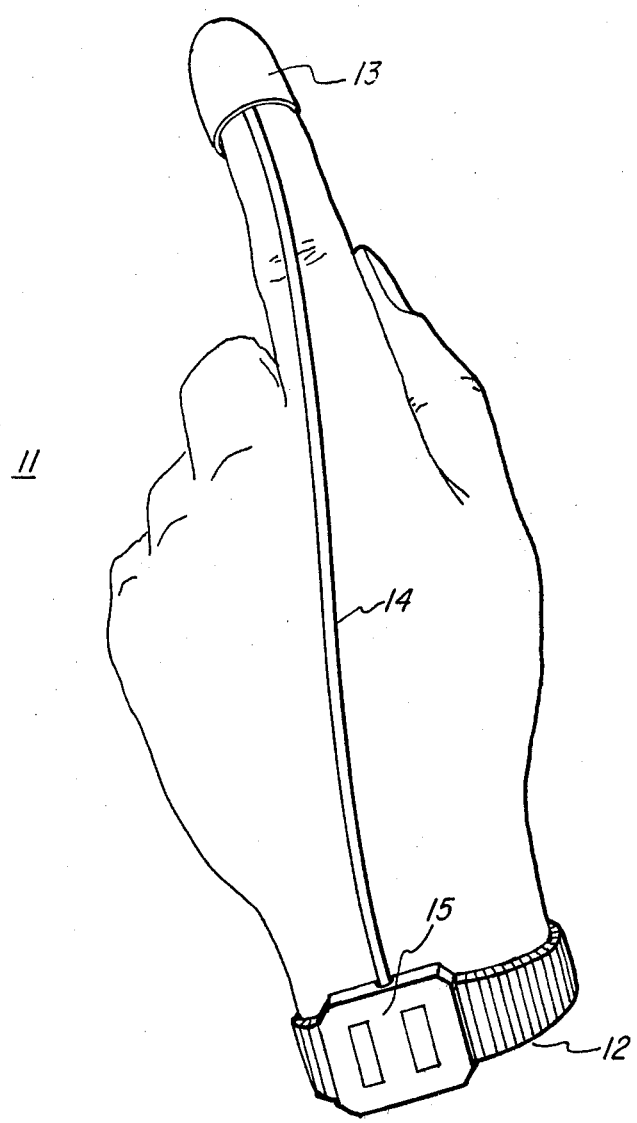
FIG. 1 is a perspective view of the biofeedback instrument of the present invention being worn by a user.

Referring to FIG. 1, a biofeedback instrument 11 of the present invention is depicted. Instrument 11 includes a wrist-mountable unit 12 and a finger-mountable unit 13, which are electrically interconnected by means of electrical wire 14. Wrist-mountable unit 12, which is of comparable size and shape to a typical wrist watch, includes the primary electronics of instrument 11 and a display 15 for displaying selected biofeedback information to a user. Wrist-mountable unit 12 further includes a temperature sensor, preferably a thermistor, disposed on the underside of wrist-mountable unit 12 for being positioned in contact with the dorsal surface of the user's wrist to sense the user's external skin temperature. Finger-mountable unit 13 includes a heart beat sensor, preferably a piezoelectric pressure transducer, for being positioned in contact with one of the user's fingers to detect the pulsing of blood caused by the user's heart beats.

Figure 2:
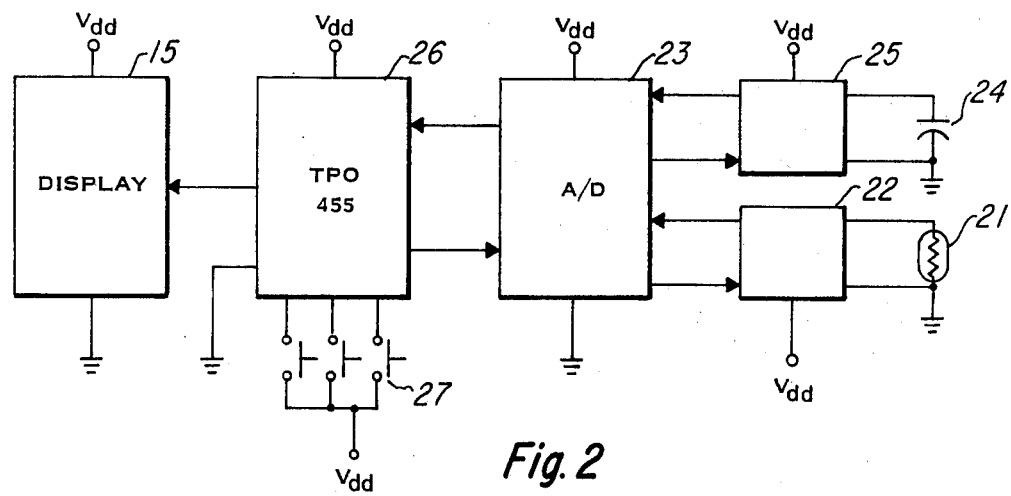
FIG. 2 is a block diagram of the major components of the biofeedback instrument of the present invention.

The major components of biofeedback instrument 11 are shown in FIG. 2. Thermistor 21 senses the user's external skin temperature and provides an analog electrical signal indicative thereof. The electrical resistance of thermistor 21 decreases with increasing skin temperature in accordance with the following equation:

$$R_T = e^{B/T}$$

where
 $R_T$ is the electrical resistance of thermistor 21
 T is user's external skin temperature in °K
 B is a material constant expressed in °K
 e is the base of the natural logarithm.

The temperature signal is then linearized and amplified by linearizing circuit 22 and transmitted to analog to digital (A/D) converter 23. Similarly, pressure sensor 24 senses the user's heart beats and generates an analog electrical signal indicative thereof. Interposed between pressure sensor 24 and A/D converter 23 is a voltage divider circuit 25 for adjusting the gain of the heart beat signal. Also, because A/D converter 23 converts only signals of positive polarity, voltage divider circuit 25 provides an input for both an original and an inverted version of the heart beat signal into A/D converter 23, so that the entire heart beat signal is converted to digital form. A/D converter 23 periodically converts the temperature signal and the original and inverted versions of the heart beat signal into respective 4-bit digital data words and transmits the digital signals to a digital processor 26, wherein the information contained in the signals is used to compute various temperature and heart beat-related biofeedback parameters, as will be described in greater detail below. Selected biofeedback information is displayed to the user on display 15, which is preferably a liquid crystal display. The mode of operation of instrument 11 and the information displayed on display 15 are controlled by the user by means of manually activatable switches 27. A battery power supply $V_{dd}$ provides electrical power for the operation of instrument 11.

Miniaturization and low power are achieved in biofeedback instrument 11 by the use of small, low power electronic components. A/D converter 23 is preferably a switch capacitor type A/D converter, such as the TL 520, manufactured by Texas Instruments Incorporated, assignee of the present invention. Switch capacitor A/D converters, which operate on the principle of transferring electrical charges among capacitors until a capacitive match is obtained, consume much less current than conventional A/D converters, which use networks of resistive elements (50–100 microamps for switch capacitor A/D converters as compared to 1–2 milliamps for resistive network A/D converters). For example, the TL 520 A/D converter, which is comprised of CMOS circuitry implemented on a single semiconductor chip, consumes approximately 50 microamps of electrical current during peak operation and is implemented on a semiconductor bar having an area on the order of 20,000 square mils. Digital processor 26 is preferably a microcomputer with on board timekeeping circuitry, such as the TPO 455, also manufactured by Texas Instruments Incorporated. Digital processor 26 is implemented on a single semiconductor chip and consumes much less current than processing circuitry used in convention AC powered, analog biofeedback instruments, wherein the processing circuitry is typically comprised of a larger number of integrated circuits and discrete components (on the order of a few hundred microamps for digital processor 26 as compared to tens of milliamps for conventional analog processing circuitry). For example, the TPO 455 microcomputer, which is comprised of low power CMOS circuitry, consumes approximately 250 microamps when fully engaged in processing information and only 14 microamps when engaged only in timekeeping operations and can be implemented on a semiconductor bar having an area of approximately 35,000 square mils. Similarly, linearizing circuit 22 is preferably comprised of a pair of low power operational amplifiers implemented in MOS technology on a single semiconductor chip. The result is that the entire biofeedback instrument 11, other than pressure sensor 24, is able to be contained within a compact, wrist-watch size casing along with a small battery power supply (preferably 3 volts). The current consumption of biofeedback instrument 22 is on the order of 600 microamps when fully engaged in processing biofeedback and on the order of 20 microamps when engaged only in timekeeping operations. A 3 volt battery will provide sufficient electrical power to operate instrument 11 for approximately 8-12 months.

Figure 3:
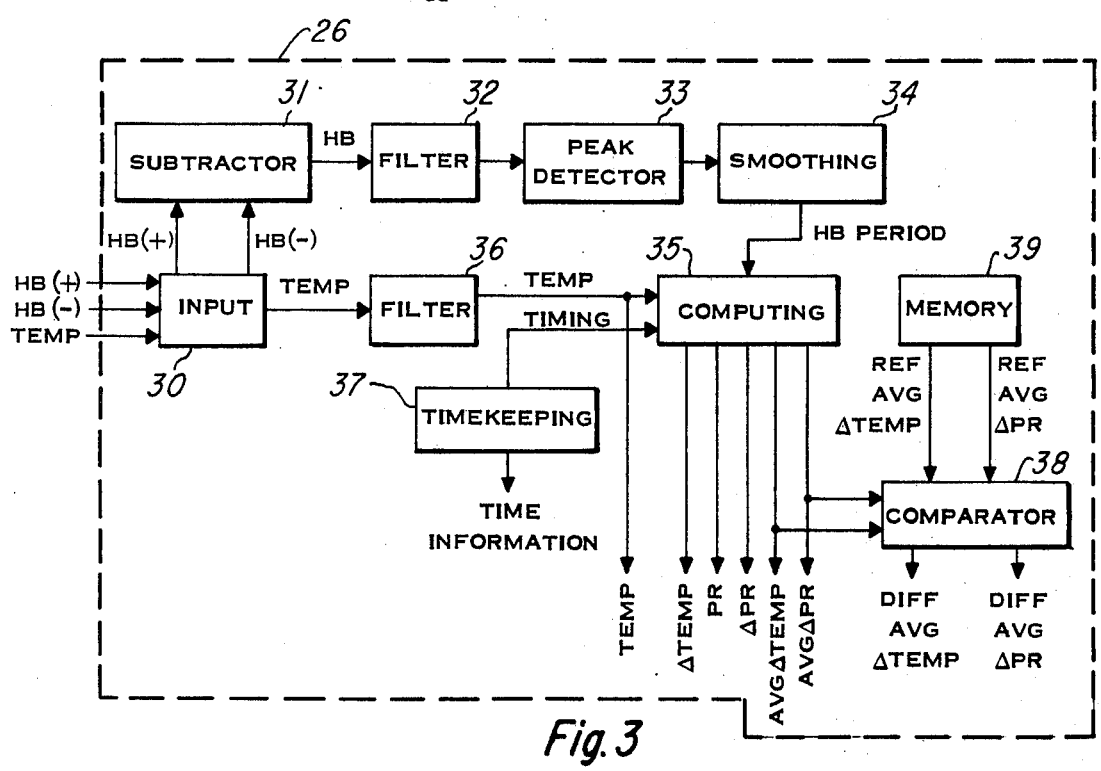
FIG. 3 is a functional block diagram of a digital processor means used in the biofeedback instrument to determine various temperature and heart beat-related biofeedback parameters.

Referring to FIG. 3, the operation of digital processor 26 is shown in detail. Digital processor 26 receives both the positive portion of the original heart beat signal HB (+), and the positive portion of the inverted heart beat signal HB(−), as well as the temperature signal TEMP, on input buffer circuit 30. The original HB (+) and the inverted HB (−) heart beat signals are then transmitted to a subtractor circuit 31 wherein the inverted heart beat signal is subtracted from the original heart beat signal to provide a signal indicative of the user's true heart beat HB. The heart beat signal is then low pass filtered by filter circuit 32 to remove noise from the signal. After the signal is low pass filtered, it resembles a sine wave. The signal is then transmitted to a peak detector circuit 33, which detects amplitude peaks in the sine wave signal. When a peak is detected, the time period elapsed since the last detected peak is computed and this value is "smoothed", i.e. averaged, together with a previous average heart beat period in a smoothing circuit 34 to yield a current average heart beat period HB PERIOD.

Peak detector circuit 33 detects both the positive and the negative peaks in the heart beat signal which occur within a aprescribed time window. The time window is referenced from the last detected peak so that when the window opens, peak detector circuit 33 begins looking for the next peak andd when the window closes, it ceases looking for a peak. The time window is chosen based upon predetermined minimum and maximum pulse rates anticipated. The elapsed time measured since the last detected positive peak and the corresponding elapsed time measured since the last detected negative peak are transmitted to smoothing circuit 34, wherein the measured elapsed times for both the positive and negative peaks are compared with corresponding elapsed times measured during a selected number of previous cycles for the respective positive and negative peaks. The elapsed time measured for the particular peak information having the lesser fluctuation over the selected cycles is selected as the value of the currently measured heart beat period. The current average heart beat period is then computed as follows: current average heart beat period = currently measured heart beat period x A + previous average heart beat period x (1−A), where A is a constant which determines the degree of smoothing of averaging.

The current average heart beat period HB PERIOD is transmitted to a computing circuit 35, wherein the user's current pulse rate is computed. The operation of peak detector circuit 33 and smoothing circuit 34 is described in greater detail in copending patent application Ser. No. 189,400 filed Sept. 22, 1980, now issued as U.S. Pat. No. 4,338,950 on July 13, 1982 which is assigned to the assignee of the present invention and is hereby incorporated herein by reference.

The skin temperature signal TEMP is filtered to remove excessive noise by filter circuit 36 and transmitted to computing circuit 35 for further processing. Computing circuit is responsive to the TEMP signal and to timing signals from timekeeping circuit 37 for computing a variety of temperature-related biofeedback parameters, including the current time rate of change in the user's skin temperature, $\Delta$ TEMP, in units of tenths of ° F. per minute, and the average time rate of change in skin temperature computed over a predetermined time period, AVG $\Delta$ TEMP. Similarly, computing circuit 35 is responsive to the HB PERIOD signal for computing the user's pulse rate, PR in units of heart beats per minute and is further responsive to timing signals from timekeeping circuitry 37 for computing various heart beat-related biofeedback parameters, including the current time rate of change in the user's pulse rate, $\Delta$ PR preferably in units of pulse rate per minute, and an average time rate of change in the user's pulse rate over a predetermined time period, AVG $\Delta$ PR.

Furthermore, digital processor 26 includes comparator circuitry 38 for comparing the average time rate of change in skin temperature and the average time rate of change in pulse rate computed over a predetermined time period with corresponding reference values for the average time rate of change in skin temperature and the average time rate of change in pulse rate, which are stored in memory circuitry 39, to provide respective differential values for the average time rates of change in skin temperature and pulse rate with respect to the reference values stored in memory 39. This gives the user an indication of how well he is progressing in being able to relax and reduce stress. The average values computed for the time rates of change in skin temperature and pulse rate and the respective differential values computed are displayed to the user at the end of a selected biofeedback monitoring period.

In addition to providing timing signals for the operation of digital processor 26, timekeeping circuitry 37 provides various time-related parameters, such as time of date and calendar date, which are selectively displayed to the user on display 15. By controlling the mode of operation of biofeedback instrument 11, all of the time information and biofeedback parameters can be selectively displayed on display 15 for the benefit of the user.

Figure 4:
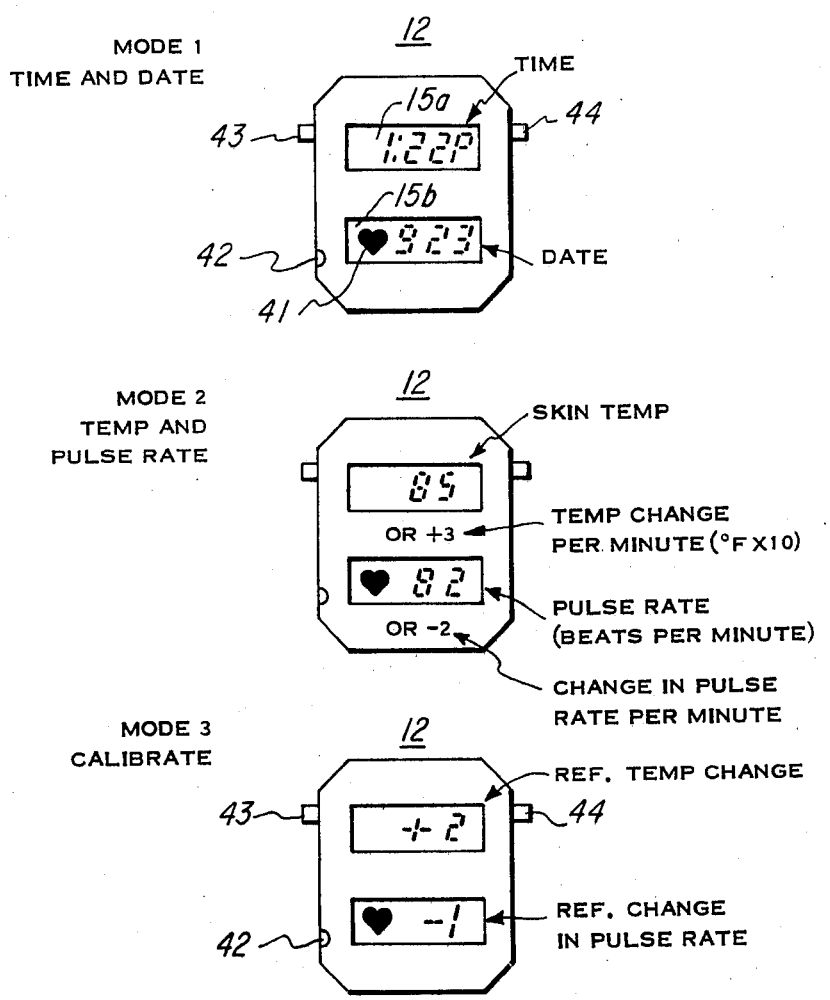
FIG. 4 is a series of front elevational views of a wrist-mountable unit of the biofeedback instrument showing the various biofeedback and time-related parameters displayed during different modes of operation of the instrument.

Referring to FIG. 4, the three modes of operation of biofeedback instrument 11 are depicted. When instrument 11 is in the TIME and DATE mode, time of day is displayed on upper display 15a and calendar date is displayed on lower display 15b. This is the normal mode of operation of instrument 11 when biofeedback parameters are not being monitored. Heart logo 41 flashes on and off in synchronism with the user's heart beat in all three modes of operation. Time of day and calendar date are set initially in accordance with the procedure typically used in calibrate an electronic timepiece. CALIBRATE/SET button 42 is pressed and START/STOP button 43 is held down until the correct time of day appears on upper display 15a. Button 42 is then pressed a second time and START/STOP button 43 is held down until the correct calendar date appears on lower display 15b.

To switch to the TEMPERATURE and PULSE RATE mode, MODE SELECT button 44 is pressed and biofeedback instrument 11 displays on upper display 25a the user's real-time external skin temperature in ° F. and on lower display 15b the user's real-time pulse rate in beats per minute. Low skin temperatures (below 90° F.) and excessive pulse rates (above 80) are indications that the user is experiencing emotional stress or trauma of some kind. The normal skin temperature and pulse rate will no doubt vary from individual to individual, with 95° F. being a typical normal skin temperature and 72 being a typical normal at rest pulse rate. If, for example, the individual's skin temperature is 85° and his pulse rate is 82, the individual is probably experiencing stress of some kind, and with the help of biofeedback instrument 11, can take the necessary steps to reduce the stress. By pressing START/STOP button 43, he can monitor his progress in reducing the stress.

When START/STOP button 43 is pressed, instrument 11 will display, at one second intervals, both the current time rate of change in the user's external skin temperature in tenths of ° F. per minute and the current time rate of change in the user's pulse rate. When the user presses START/STOP button 43 a second time, instrument 11 ceases displaying the current time rates of change in skin temperature and pulse rate and displays the average time rates of change in skin temperature and pulse rate computed over the previous monitoring period. Also, the respective differential values for the time rates of change in skin temperature and pulse rate with respect to the stored reference values are displayed.

To switch to the CALIBRATION mode of operation, the user presses MODE SELECT button 44 again. The reference values stored in system memory for the average time rates of change in skin temperture and pulse rate are displayed to the user on upper and lower displays 15a and 15b, respectively. If the user desires to input new reference values, he pushes START/STOP button 43, thereby causing instrument 11 to begin monitoring the user's skin temperature and pulse rate, as described above with reference to the TEMPERATURE and PULSE RATE mode. Instrument 11 will display, at one second intervals, the current time rates of change in skin temperature and pulse rate until the user presses START/STOP button 43 a second time. Instrument 11 then ceases monitoring skin temperature and pulse rate and displays the average time rates of change in skin temperature and pulse rate computed during the calibration period. These newly computed average values are stored in memory as the new reference values. Alternatively, the user can set in selected reference values by pressing CALIBRATE/SET button 42 and holding down START/STOP button 43 until the desired reference value for the average time rate of change in skin temperature appears on upper display 15a and then pressing CALIBRATE/SET button 42 again and holding it down until the desired reference value for the average time rate of change in pulse rate appears on lower display 15b.

The biofeedback instrument of the present invention provides a low power, miniature instrument for computing various physiological and biofeedback parameters of interest to the user. Such parameters include the user's external skin temperature and pulse rate and time rates of change in skin temperature and pulse rate and give the user an indication of when he is experiencing emotional or physiological stress and how well he is able to consciously relax and reduce the stress.

Various embodiments of the invention have now been described in detail. Since it is obvious that many additional changess and modifications can be made to the above-described details without departing from the nature and spirit of the invention, the invention is not to be limited to the these details except as set forth in the appended Claims.

What is claimed is:

1. A body-mountable instrument for providing biofeedback information pertaining to the human body of a user thereof, said instrument comprising:
　temperature sensing means adapted to be disposed in contact with the body of a living human for detecting the external skin temperature of the human body and providing a temperature signal output indicative of the magnitude thereof;
　heart beat sensing means adapted to be disposed in contact with the body at an appropriate location thereon for detecting the heart beats of the human body and providing a heart beat signal indicative thereof;
　processing means including:
　　time-keeping means for keeping track of the elapsed time,
　　means operably coupled to said temperature sensing means and periodically at predetermined time intervals of a constant multiple within the elapsed time as established by said time-keeping means operating upon said temperature signal output of said temperature sensing means for determining a time rate of change in the external skin temperature of the human body over a predetermined time interval and producing an informational biofeedback output signal indicative thereof,
　　means operably coupled to said heart beat sensing means and responsive to said heart beat signal and elapsed time for determining the current pulse rate and the time rate of change in the pulse rate of the human body over a predetermined time interval and producing additional informational biofeedback output signals respectively indicative thereof,
　　said processing means being operable during a selected monitoring period to periodically determine the current time rates of change in the external skin temperature and the pulse rate of the human body, and means for determining average values for the time rates of change in the external skin temperature and the pulse rate of the human body for said monitoring period at the end thereof and producing another informational biofeedback output signal indicative thereof; and presentation means operably coupled to said processing means, said presentation means being responsive to said informational biofeedback output signals for providing a real-time indication of the external skin temperature of the human body at any given time instant and the time rate of change in the external skin temperature of the human body, a real-time indication of the pulse rate of the human body at any given time instant and the time rate of change in the pulse rate of the human body, and an indication of said average values for the time rates of change in the external skin temperature and the pulse rate of the human body during said monitoring period.

2. An instrument as set forth in claim 1 wherein said processing means further includes memory means in which reference values for the time rates of change in external skin temperature and the pulse rate of the human body are stored, and means for determining respective differences between said determined average values and corresponding reference values, the differences being indicative of the relative progress of the user of the instrument in reducing stress.

3. An instrument as set forth in claim 2, further including operator input means operably coupled to said processing means and said memory means thereof for introducing data thereinto, said reference values for the time rates of change in external skin temperature and the pulse rate of the human body as stored in said memory means of said processing means being directly input thereto by the user of the instrument via said operator input means or alternatively being input to said memory means by said processsing means as determined during a selected calibration period.

4. A method of providing a user with biofeedback information indicative of the level of stress he is experiencing and his progress in reducing the stress, comprising the steps of:

at least periodically detecting the user's external skin temperature;

detecting the user's heart beat;

providing time keeping circuitry for keeping track of elapsed time and determining a time rate of change in the user's external skin temperature over a predetermined time interval based on the periodically detected external skin temperatures and elapsed time information;

computing the user's pulse rate in response to the detected heart beats and elapsed time and determining a time rate of change in the pulse rate over a predetermined time interval;

further determining at the end of a selected monitoring period average values for the time rates of change in external skin temperature and pulse rate for said monitoring period; and providing a real-time indication to the user of his external skin temperature and the time rate of change in his external skin temperature, a real-time indication of the pulse rate of the user at any given time instant and the time rate of change in the pulse rate of the user, and an indication of said average values for the time rates of change in the external skin temperature and the pulse rate of the user during said monitoring period.

5. The method according to claim 4 further including the step of comparing said determined average values with predetermined reference values for the time rates of change in external skin temperature and pulse rate and determining the respective differences therebetween, said differences representing the relative progress made by the user in being able to reduce stress.

* * * * *